US00PP11093P

United States Patent [19]

Fuess

[11] Patent Number: Plant 11,093

[45] Date of Patent: Oct. 12, 1999

[54] CHRYSANTHEMUM PLANT NAMED 'EMPIRE ECLIPSE'

[76] Inventor: Janet S. Fuess, 22 Country Club Dr., New York Mills, N.Y. 13417

[21] Appl. No.: 09/035,952

[22] Filed: Mar. 6, 1998

[51] Int. Cl.[6] ..... A01H 5/00

[52] U.S. Cl. ..... Plt./290

[58] Field of Search ..... Plt./287, 289, 290, Plt./291

*Primary Examiner*—Howard J. Locker
*Attorney, Agent, or Firm*—Foley & Lardner

[57] ABSTRACT

A new and distinct cultivar of Chrysanthemum plant named 'Empire Eclipse', characterized particularly by its peach/coral color with darker center; exceptionally large capitulum size of 6.0–6.5 cm; fully expanded ray florets 2.5 cm long and 0.7 cm wide; 7½ week flower response in controlled light/shade programs; natural season flowering date of September 18; and semi-upright cushion habit.

1 Drawing Sheet

The present invention comprises a new and distinct cultivar of *Dendranthema grandifora morifolium,* referred to by the cultivar name 'Empire Eclipse'.

'Empire Eclipse' is a product of a planned breeding program which had the objective of creating new Chrysanthemum cultivars with freely branching cushion habit, large peach/coral decorative capitulum type, early flower response, and suitability as a garden variety. Such traits in combination were not present in previously available commercial cultivars.

'Empire Eclipse' was originated from a hybridization made by the inventor in a controlled breeding program in New Hartford, N.Y., in 1993. The female parent was 'Empire Cabernet', disclosed in U.S. Plant Pat. No. 9,927. The male parent of 'Empire Eclipse' was a pink decorative seedling identified as B88-2, a proprietary breeding line.

'Empire Eclipse' was discovered and selected as one flowering plant within the progeny of the stated parentage by the inventor in September 1994 in a controlled environment in New Hartford, N.Y.

The first act of asexual reproduction of 'Empire Eclipse' was accomplished when vegetative cuttings were taken by the inventor from the initial selection in October 1994 in a controlled environment in New Hartford, N.Y. Horticultural examination of selected units initiated in September 1995 has demonstrated that the combination of characteristics as herein disclosed for 'Empire Eclipse' are firmly fixed and are retained through successive generations of asexual reproduction.

'Empire Eclipse' has not been observed under all possible environmental conditions. The phenotype may vary significantly with variations in environment such as temperature, light intensity, and day length, without, however, any variation in genotype. The following observations, measurements and comparisons describe plants grown in New Hartford, N.Y. under natural outdoor conditions which approximate those generally used in commercial practice.

The following traits have been repeatedly observed and are determined to be basic characteristics of 'Empire Eclipse', which in combination distinguish this chrysanthemum as a new and distinct cultivar:

1. An unusual peach/coral ray floret color with a darker center, presenting a pleasing bicolor effect, even as flower ages.
2. An exceptionally large capitulum size of 6.0–6.5 cm as compared to other garden mums.
3. An average of 312 ray florets and 34 disc florets per flower.
4. Fully expanded ray florets are 2.5 cm long and 0.7 cm wide.
5. 7½ week flower response in controlled light/shade programs.

6. Natural season flowering date of September 18 in New Hartford, N.Y.
7. Semi-upright cushion habit.

Of the many commercial cultivars known to the present inventor, the most similar in comparison to 'Empire Eclipse' is the female parent, 'Empire Cabernet'. In comparison to 'Empire Cabernet', 'Empire Eclipse' flowers ½ week later in light/shade programs and approximately 4–5 days earlier in natural season, and has a completely different capitulum tonality (peach/coral, compared to purple). The large capitulum size, semi-upright cushion habit, pleasing bicolor effect and overall plant height are similar to those same characteristics of 'Empire Cabernet'.

The accompanying photographic drawing comprises a top perspective view showing typical flower and foliage characteristics of 'Empire Eclipse', with colors being as nearly true as possible with illustrations of this type.

In the following description color references are made to The Royal Horticultural Society Colour Chart. The color values were determined between 10:00 am and 2:00 pm on Sep. 25, 1997 under 4,000 footcandles at New Hartford, N.Y.

Classification:

*Botanical.*—*Dendranthema grandiflora* cv. 'Empire Eclipse'.

*Commercial.*—Flat decorative garden mum.

Inflorescence:

*Capitulum.*—Form: Decorative. Type: Flat. Diameter Across Face: 6.0–6.5 cm.

*Corolla of ray florets.*—Color (General tonality from a distance of three meters: Peach/coral. Color (under surface): 35D. Color (upper surface): 27A, fading to 27B around outer edge of capitulum; 179B, fading to 179C at center of capitulum.

*Corolla of disc florets.*—Color (mature): 4A. Color (immature): 144B.

*Reproductive orgams.*—Androecium: Present on disc florets only, no pollen. Gynoecium: Present on both ray and disc florets.

Plant:

*General appearance.*—Height: 25–35 cm, when grown in 8" pot, outdoors, with no growth regulators.

*Forliage.*—Color (under surface): 138A. Color (upper surface): 137B. Shape: 6.0–7.0 cm long, 4.5–5.0 cm wide, five-lobed with minute point at tip.

It is claimed:

1. A new and distinct cultivar of Chrysanthemum plant named 'Empire Eclipse', as illustrated and described.

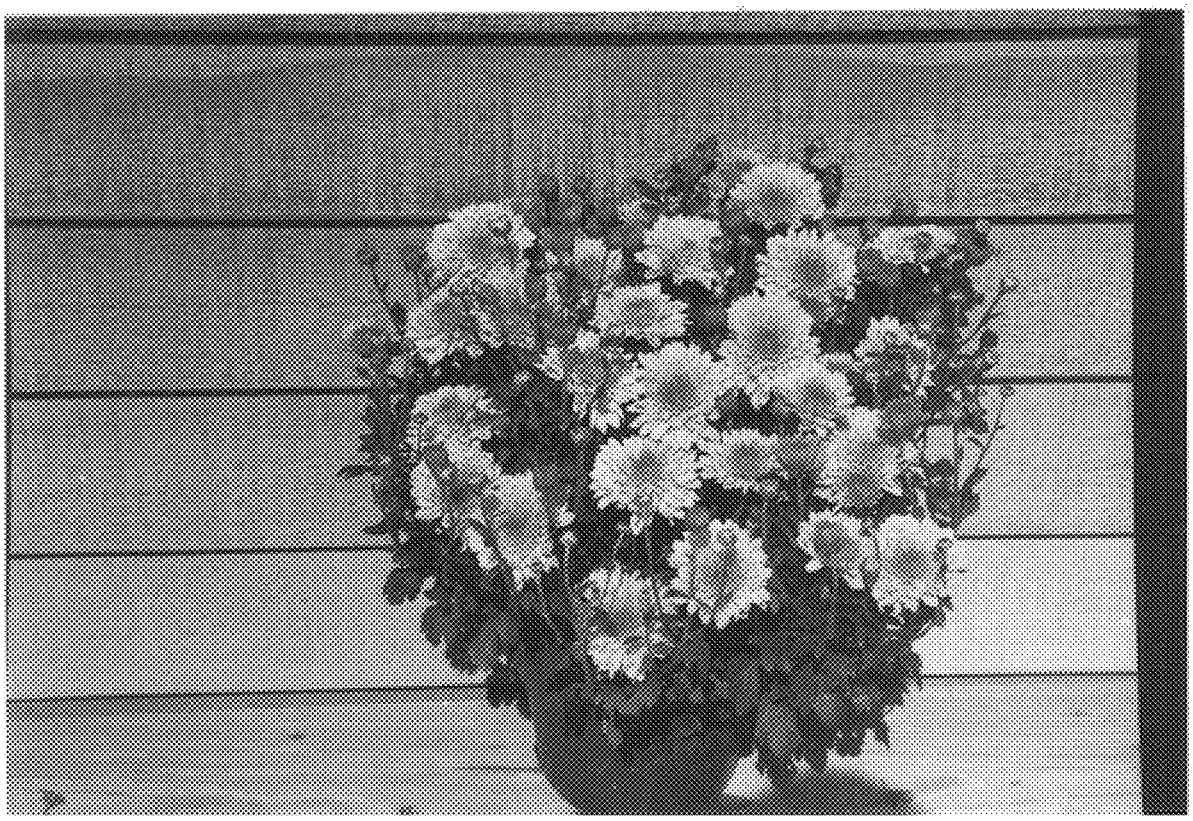

* * * * *